United States Patent
Graumann

[19]

[11] Patent Number: 6,120,180
[45] Date of Patent: Sep. 19, 2000

[54] X-RAY EXPOSURE SYSTEM FOR 3D IMAGING

[75] Inventor: Rainer Graumann, Hoechstadt, Germany

[73] Assignee: Siemens Aktiengesellschaft, Munich, Germany

[21] Appl. No.: 09/174,522

[22] Filed: Oct. 16, 1998

[30] Foreign Application Priority Data

Oct. 17, 1997 [DE] Germany .......................... 197 46 093

[51] Int. Cl.[7] .................................................. A61B 6/08
[52] U.S. Cl. .......................................... 378/206; 378/197
[58] Field of Search .................................... 378/205, 206, 378/197

[56] References Cited

U.S. PATENT DOCUMENTS

| | | |
|---|---|---|
| 4,791,934 | 12/1988 | Brunnett . |
| 5,109,397 | 4/1992 | Gordon et al. . |
| 5,512,761 | 4/1996 | Winkelmann . |
| 5,706,324 | 1/1998 | Wiesent et al. . |
| 5,772,594 | 6/1998 | Barrick .................................... 378/198 |
| 6,007,243 | 12/1999 | Ergun et al. ............................ 378/205 |

FOREIGN PATENT DOCUMENTS

| | | |
|---|---|---|
| 36 04 955 | 8/1987 | Germany . |
| 90 17 443 | 4/1991 | Germany . |
| 94 08 562 U | 9/1994 | Germany . |
| 195 35 583 | 3/1997 | Germany . |
| WO 91/079913 | 6/1991 | WIPO . |

*Primary Examiner*—Craig E. Church
*Attorney, Agent, or Firm*—Hill & Simpson

[57] ABSTRACT

X-ray system has an X-ray apparatus on which an X-ray source and an X-ray reception receiver mounted so as to be adjustable relative to an examination subject for registering 2D projections of a region of the subject with subsequent 3D image reconstruction of the region of the subject, the X-ray apparatus carrying transmission and reception devices for acoustic waves or electromagnetic waves for determining projection angles that belong to the individual 2D projections and are required for the 3D image reconstruction, the transmission or the reception devices being co-moved with the X-ray system.

20 Claims, 1 Drawing Sheet

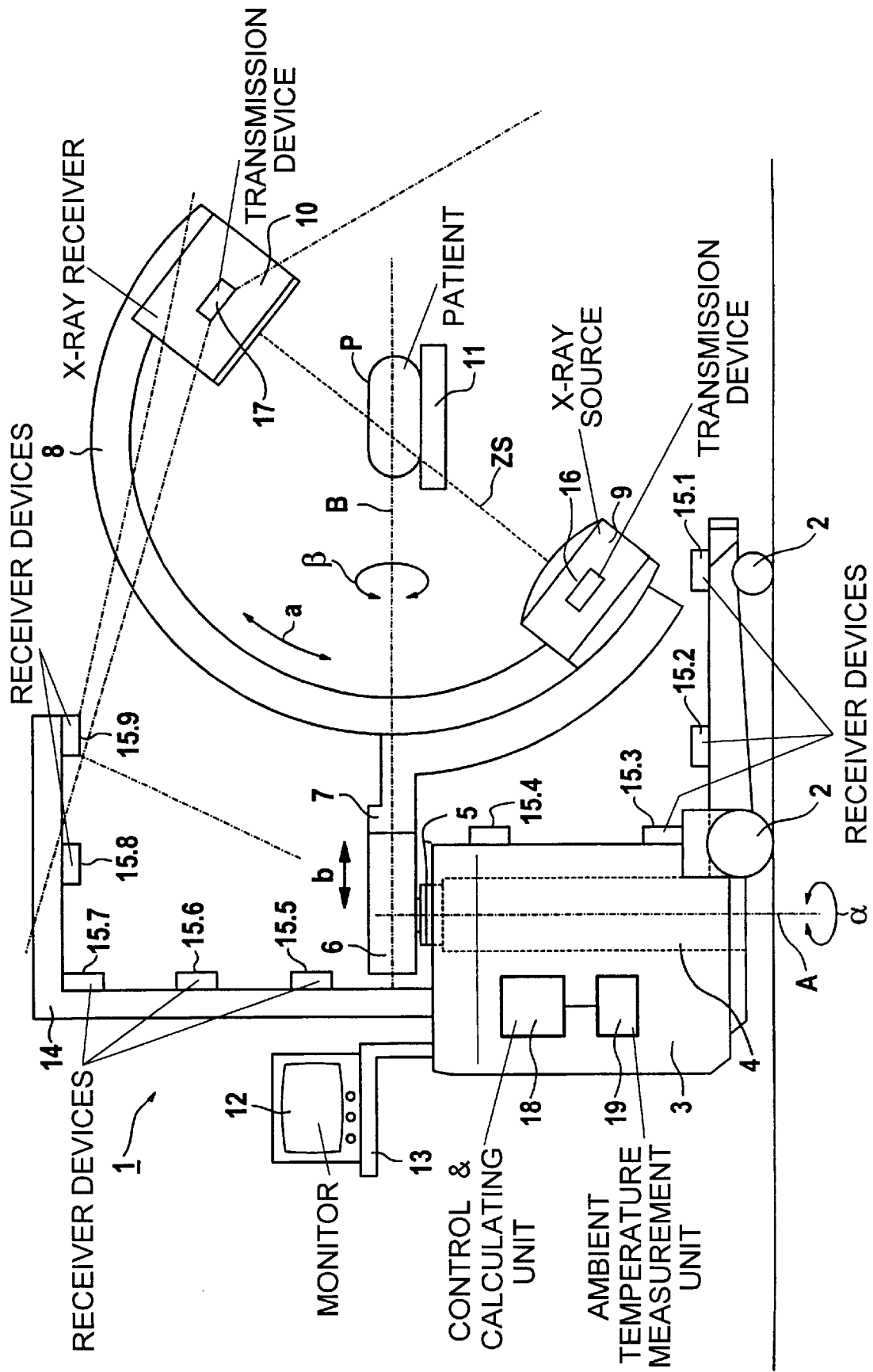

X-RAY EXPOSURE SYSTEM FOR 3D IMAGING

BACKGROUND OF THE INVENTION

1. Field of the Invention

The present invention is directed to an X-ray system with an X-ray apparatus including an X-ray source and an X-ray receiver that is adjustable relative to a subject to be examined for registering 2D projections of a region of the subject, with subsequent 3D image reconstruction of the subject.

2. Description of the Prior Art

An X-ray system of the above type usually has a C-arm for carrying the X-ray source and the X-ray receiver, this C-arm being seated such in a holder at the X-ray system so that it is motor-adjustable in a specific angular range along its circumference (orbital motion). For acquiring 2D projections from different projection angles for 3D image reconstruction of, for example, a body region of a subject with the assistance of the C-arm X-ray system, the C-arm—after appropriate placement relative to the subject—is adjusted along its circumference during the registration of 2D projections of the body region of the subject. 3D images of the body region of the life form are subsequently reconstructed from the 2D projections registered with the X-ray system during the adjustment motion of the C-arm. The 3D reconstruction, however, assumes exact knowledge of the projection geometry, i.e. the knowledge of the position of the X-ray source and the X-ray receiver during each of the individual 2D projections.

Known stationary and particularly mobile C-arm X-ray systems exhibit mechanical instabilities particularly relating to the adjustment of the C-arm along its circumference, causing deviations of the real adjustment motion of the C-arm from the ideal adjustment motion to occur. The determination of the projection angles is thus often affected by errors, the quality of the 3D images reconstructed from the 2D projections suffering therefrom.

The following two methods are known for avoiding errors in the determination of the projection angles.

German OS 195 12 819 discloses the use of a marker ring usually formed of plexiglass with inserted metal structures, that is arranged around the body region of the subject to be examined. The metal structures of the marker ring are visible in the 2D projections of the body region to be examined, so that the respective projection angles of the 2D projections can be calculated from their position. This method, however, has the disadvantage that the marker ring has a relatively large diameter, so that the spacing between the X-ray source and the marker ring is very small (a few centimeters) given C-arm with a small diameter. The metal structures therefore appear extremely enlarged in the 2D projections, so that large parts of the 2D projections are overlaid by the metal structures. Further, only a small region of the metal structures of the marker ring is imaged in the 2D projections, so that the determination of the projection angles is difficult on the basis of the slight number of imaged metal structures.

Calibration measurements can be made before the actual patient measurement, assuming that the system behavior, i.e. essentially the adjustment motions of the C-arm, is reproducible to a high degree. This method, however, is extremely time-consuming and, moreover, can only be applied with a mechanically reinforced, stationary C-arm X-ray apparatus. Application to mobile X-ray apparatus is not possible because of the aforementioned mechanical instability of such an X-ray apparatus. Mechanical stabilization of a mobile X-ray apparatus is not possible because of the great increase in weight that limits the mobility.

U.S. Pat. No. 5,109,397 discloses a mobile computed tomography system having an X-ray system rotating around a rotation center and including an X-ray source and an X-ray receiver, to which sensors are allocated. These sensors move along with the X-ray system and interact with a stationary ring allocated to the rotation center for detecting lateral movements of the X-ray system during a scan. The sensors generate signals which are evaluated to allow the spacings between their defined points of attachment and the ring to be determined. The acquired data are subsequently utilized in the reconstruction of tomograms. The ring is thereby arranged in the propagation path of an X-ray beam emanating from the X-ray source.

Sensors for determining the distance of two objects from one another are also disclosed in German PS 43 32 254 and German Utility Model 94 08 562. The determination of the distance ensues by measuring the transit time of acoustic waves or electromagnetic waves.

German OS 36 04 955 discloses an X-ray diagnostic apparatus having an image generating system with an X-ray radiator and a radiation receiver as well as a patient table. Position sensors in the form of potentiometers that acquire the position of adjustable components of the image generating system are connected to these components.

German OS 195 35 583 also discloses an X-ray diagnostics apparatus with a positioning aid. A light transmitter for emitting a light beam is provided at the X-ray image intensifier so that this light beam is focused onto a X-ray radiator disposed opposite the X-ray image intensifier. In this way, a positioning of the X-ray radiator and the X-ray image intensifier can ensue with reference to an examination subject without emitting X-rays.

SUMMARY OF THE INVENTION

An object of the present invention is to provide an X-ray system of the type initially described wherein the determination of the projection angles is simplified and is suitable for a stationary as well as for a mobile X-ray apparatus.

This object is inventively achieved in an X-ray system with an X-ray apparatus having an X-ray source and an X-ray receiver that is adjustable relative to an examination subject for registering 2D projections of a region of the subject, with subsequent 3D image reconstruction of the region of the subject, wherein the X-ray system—for determining projection angles belonging to the individual 2D projections that are required for the 3D image reconstruction—has transmission and reception devices for acoustic waves or electromagnetic waves, and wherein the transmission or the reception devices are co-moved with the X-ray system and are arranged in the region of the X-ray source and the X-ray receiver, and the reception devices or the transmission devices can be arranged at stationary parts of the X-ray apparatus with reference to the X-ray system. For example, reception devices can be arranged at stationary parts of the X-ray apparatus and transmission devices are arranged in the region of the X-ray source and of the X-ray receiver, the transmission devices being co-moved with the X-ray source and the X-ray receiver during the course of an adjustment motion of these components. During the adjustment motion of the X-ray system with simultaneous registration of 2D projections from different projection angles, the transmissions devices preferably emit acoustic waves, light waves or microwaves per registration of a 2D projection that are received by the reception devices. The evaluation of the received acoustic, light or microwaves subsequently enables the determination of the exact position of the X-ray source and the X-ray receiver during the registration of a corresponding 2D projection, so that the projection angles of each of the 2D projections can be calculated from the respectively identified positions of the X-ray source and of the X-ray receiver. Due to their small dead weight and their small structural size, the transmission and reception devices for determining the projection angles of the 2D projections are employable in a stationary as well as a mobile X-ray apparatus, so that the capability of 3D imaging is also available for a mobile X-ray apparatus.

In a version of the invention the transmission and/or reception devices exhibit such a directional characteristic such that the acoustic waves or electromagnetic waves emitted by the transmission devices during the adjustment motion of the X-ray system are received by each of at least two reception devices. By employing transmission devices with such a directional characteristic, the required transmission power of the transmission devices is reduced compared to transmission devices without a directional characteristic (isotropic radiators). The reception of noise signals is reduced by employing reception devices with a directional characteristic, which simplifies the signal processing.

In a preferred embodiment of the invention, the X-ray system has a control and calculating unit that determines the phases and/or transit times of the acoustic waves or electromagnetic waves between transmission and reception devices for determining the projection angles. The phase and/or transit time data are thereby interpreted such that the path lengths between transmission devices and reception devices can be determined with a precision of $\lambda/4$ through $\lambda/8$ according to known calculating methods for each position of the X-ray source and of the X-ray receiver in a 2D projection. Subsequently, the projection angles of the respective 2D projections for the reconstruction of 3D images are acquired of each 2D projection for the positions of the X-ray source and of the X-ray receiver identifiable from the path lengths. For example, the positions of the X-ray source and of the X-ray receiver can be calculated with reference to a stationary Cartesian coordinate system.

In a further version of the invention, the transmission devices emit acoustic waves or electromagnetic waves differing in frequency. An unambiguous identification of the source of a received acoustic wave or electromagnetic wave, i.e. which transmission device emitted the wave, is possible in this way, so that the determination of the path length between a transmission and reception device required for the determination of the projection angle can ensue exactly and free of confusion.

In another version of the invention, a unit for measuring the ambient temperature is provided since, for example, the transit time of acoustic waves is dependent on the ambient temperature. In this way, the current ambient temperature is known, so that the path length corresponding to a transit time of the sound can be exactly determined dependent on the current ambient temperature.

In a preferred embodiment of the invention, the transmission devices are ultrasound transmitters and the reception devices are ultrasound receivers that are commercially available at a reasonable cost. Their signals can be evaluated for determining the position of the X-ray source and the X-ray receiver so that the projection angles can be identified with a precision adequate for the reconstruction of 3D images.

In another embodiment of the invention, the X-ray source and the X-ray receiver are arranged at the ends of a C-arm, the X-ray source and the X-ray receiver each carrying a transmission device and the X-ray system has a number of reception devices arranged dispersed around the system structure. The arrangement of a transmission device at each of the X-ray source and the X-ray receiver is adequate for the determination of the spatial coordinates in the stationary coordinate system that indicate the position of the X-ray source and of the X-ray receiver in a 2D projection.

DESCRIPTION OF THE DRAWING

The single FIGURE is a schematic illustration of an X-ray exposure system for 3D imaging, constructed in accordance with the principles of the present invention.

DESCRIPTION OF THE PREFERRED EMBODIMENTS

In the present exemplary embodiment, the inventive X-ray system has a C-arm X-ray apparatus 1 with a mobile cart 3 movable on wheels 2. The C-arm X-ray apparatus 1 has a lifting mechanism 4 that is only schematically indicated in the FIGURE, with a column 5 having a longitudinal axis A around which the column 5 can be rotated in the direction of the double arrow α. A holder 6 is arranged at the column 5, a bearing part 7 for mounting a C-arm 8 being in turn arranged at the holder 6. The C-arm 8 has an X-ray source 9 and an X-ray receiver 10 lying opposite one another at its two ends, that are arranged relative to one another so that a central ray ZS of an X-ray beam emanating from the X-ray source 9 strikes the X-ray receiver 10 approximately centrally. In a known way, the C-arm 8 is seated at the bearing part 7 so as to be adjustable manually or motor-driven in the direction of the double arrow a along its circumference in a way not shown in greater detail. In a known way, the bearing part 7 is rotatable around a common axis B of the holder 6 and the bearing part 7 (see the double arrow β, angulation) and is seated at the holder 6 so as to be displaceable in the direction of the axis B (see double arrow b). With the assistance of the lifting device 4, the C-arm 8, which is connected to the column 5 of the lifting device 4 via the bearing part 7 and the holder 6, is vertically adjustable relative to the cart 3.

In the present exemplary embodiment, the C-arm X-ray apparatus 1 is provided for producing 3D images of a body region of a patient P (only schematically shown in the FIGURE) lying on a patient bed 11. The 3D images are reconstructed from 2D projections of the body region from different projection directions that are acquired with the X-ray source 9 and the X-ray receiver 10 and can be displayed with a monitor 12 that is arranged on a holder 13 of the C-arm X-ray apparatus 1.

For registering 2D projections from different projection angles, the C-arm 8 is motor-adjusted along its circumference in the direction of the double arrow a in an angular range of approximately 200° around the body region of the patient P to be examined and visually displayed, with approximately 50 through 100 2D projections of the body region of the patient P being registered from different projection directions.

For the exact determination of the different projection angles of the 2D projections—which are absolutely necessary for the 3D image reconstruction of the body region of the patient from the 2D projections—the C-arm X-ray apparatus 1 has a number of reception devices arranged at the cart 3, which is stationary relative to the C-arm 8, and at a stationary mounting bracket 14 of the cart 3. In the present exemplary embodiment, the reception devices are ultrasound receivers 15.1 through 15.9. The X-ray source 9 as well as the X-ray receiver 10 are each provided with respective transmission devices in the form of ultrasound transmitters 16 and 17 that are co-moved with the X-ray system given the adjustment motion of the C-arm 8 along its circumference. The ultrasound receivers 15.1 through 15.9 are attached to the cart 3 and the bracket 14 so that an unobstructed line of sight of the ultrasound transmitters 16, 17 to at least two of the ultrasound receivers 15.1 through 15.9 always exits during the adjustment motion of the C-arm 8.

A control and calculating unit 18 of the C-arm X-ray apparatus 1, which both controls the motor-adjustment of the C-arm 8 and triggers the registration of 2D projections, also controls the triggering of ultrasound waves of the ultrasound transmitters 16 and 17, that ensues simultaneously with the triggering of a 2D projection. In this way, the corresponding position of the X-ray source 9 and the X-ray receiver 10, and thus the respective projection angle, can be determined for every 2D projection. The signal lines for the transmission of the control signals for the motor-adjustment of the C-arm 8, for triggering 2d projections and for triggering ultrasound waves are not shown in the FIGURE.

The ultrasound transmitters 16 and 17 can be operated with different frequencies in the region of approximately 200 kHz so that the ultrasound waves received by the ultrasound receivers 15.1 through 15.9 can be unambiguously allocated to one of the ultrasound transmitters 16 or 17.

The ultrasound transmitters 16, 17 and the ultrasound receivers 15.1 through 15.9 exhibit directional characteristics matched to the adjustment motion of the X-ray system that are shown with dot-dash lines in the figure for the ultrasound receiver 15.9 and the ultrasound transmitter 17, as an example. In this way, the reception of foreign (extraneous) signals by the ultrasound receivers 15.1 through 15.9 that disturb the signal evaluation can be reduced, and the required transmission power of the ultrasound transmitters 16, 17 can be reduced compared to isotropically emitting (radiating) ultrasound transmitters.

For determining the respective positions of the X-ray source 9 and the X-ray receiver 10 in 2D projections relative to a stationary coordinate system, for example a Cartesian coordinate system, it is necessary that at least two of the ultrasound receivers 15.1 through 15.9 receive ultrasound waves from the ultrasound transmitters 16 and 17 allocated to the X-ray source 9 and the X-ray receiver 10 during the adjustment motion of the C-arm 8.

The ultrasound waves received by the ultrasound receivers 15.1 through 15.9 are subsequently supplied to the control and calculating unit 18 that determines the phases and/or the transit times of the respective ultrasound waves belonging to a 2D projection. Since the transit time of the ultrasound is dependent on the ambient temperature, the C-arm X-ray apparatus 1 also has a unit 19 for measuring the ambient temperature, which is taken into consideration in compensation calculations in the determination of the transit time of the ultrasound.

On the basis of the phase and/or transit time information of the received ultrasound waves, the control and calculating unit 18 calculates the respective path lengths between the X-ray source 9 or the X-ray receiver 10 and at least two of the ultrasound receivers 15.1 through 15.9, functioning as points of reference that have received the corresponding ultrasound waves for each 2D projection. The respective positions of the X-ray source 9 and of the X-ray receiver 10 with reference to the stationary coordinate system, and thus the projection angle belonging to each 2D projection required for the reconstruction of 3D images, can be exactly determined for each 2D projection on the basis of the path lengths determined during the adjustment motion of the C-arm 8 and the known positions of the ultrasound receivers 15.1 through 15.9 in the stationary coordinate system. The projection angles determined in this way are then utilized for the reconstruction of 3D images of body regions of the patient P that, as already mentioned, can be displayed on the monitor 12 of the C-arm X-ray apparatus 1.

The position of the X-ray source 9 and of the X-ray receiver 10 can be determined with a precision of $\lambda/4$ through $\lambda/8$ of the ultrasound wavelength employed using known calculating methods. Given employment of ultrasound with a frequency of 200 kHz and a wavelength of the ultrasound waves of approximately $\lambda=1.7$ mm, the precision of the position determination thus amounts to 0.425 through 0.2125 mm.

The directional characteristic of the ultrasound receiver 15.9 and of the ultrasound transmitter 17 shown in the figure is only an example. Each of the ultrasound transmitters 16, 17 or each of the ultrasound receivers 15.1 through 15.9 can exhibit a different directional characteristic that is preferably matched to the adjustment motion of the X-ray system in 2D projections.

The number of ultrasound transmitters and ultrasound receivers provided for the position determination of the X-ray source 9 and the X-ray receiver 10 can deviate from the number shown in the exemplary embodiment. Further, the described attachment of the ultrasound transmitters and ultrasound receivers to the C-arm X-ray apparatus 1 is merely exemplary and can also be differently implemented. For example, the reception devices can also be arranged at the X-ray source 9 and the X-ray receiver 10 and the transmission devices can be arranged at the cart 3 and the bracket 14.

For examining body regions of a subject, the C-arm 8 with the ultrasound transmitters 16 and 17 can also be tilted (angulation) around the axis B from a different position than that described in the present exemplary embodiment and can be turned around the axis A with the lifting mechanism 4. In order to be able to determine the projection angles as well during the 2D projections, i.e. during the adjustment motion of the C-arm 8, in this case, i.e. in order to assure the reception of the ultrasound waves, the ultrasound receivers 15.1 through 15.9 must also be tilted and turned corresponding to the tilt and rotation of the C-arm 8 due to the directional characteristics of the ultrasound transmitters 16, 17 and the ultrasound receivers 15.1 through 15.9. In this case, for example, the bracket 14 is mounted so that it follows the tilting and rotation of the C-arm 8.

In the present exemplary embodiment, the X-ray source 9 and the X-ray receiver 10 are each provided with only one ultrasound transmitter 16, 17, enabling the determination of the respective positions of the X-ray source 9 and the X-ray receiver 10 in the orbital plane (plane of the adjustment motion of the C-arm). When the X-ray source 9 and the X-ray receiver 10 are provided with at least two ultrasound transmitters, then the determination of the angle of inclination of the X-ray source 9 and the X-ray receiver 10 is also possible in the angulation direction with reference to the isocenter (not shown in the figure) of the C-arm 8. Such angles of inclination occur due to the aforementioned instabilities of the C-arm X-ray apparatus, particularly during the adjustment motion of the C-arm 8.

Transmitters and receivers that operate on the basis of other acoustic waves or electromagnetic waves, for example microwaves or light, can be provided for the position determination of the X-ray source 9 and the X-ray receiver 10 instead of the ultrasound transmitters 16, 17 and the ultrasound receivers 15.1 through 15.9.

The invention was explained herein with reference to the example of a mobile C-arm X-ray apparatus 1. The employment of the transmission and reception devices for the position determination of the X-ray source 9 and the X-ray receiver 10, however, is not limited to use in mobile C-arm X-ray apparatus but is also possible in a stationary X-ray apparatus.

Although modifications and changes may be suggested by those skilled in the art, it is the intention of the inventor to embody within the patent warranted hereon all changes and modifications as reasonably and properly come within the scope of his contribution to the art.

I claim as my invention:

1. An X-ray exposure system comprising:

an X-ray source which emits an X-ray beam;

an X-ray receiver on which said X-ray beam is incident;

a carrier to which said X-ray source and said X-ray receiver are mounted;

holder means to which said carrier is movably mounted for moving said X-ray source and said X-ray receiver relative to an examination subject for obtaining a plurality of successive 2D projections of said examination subject respectively from a plurality of different projection directions, each of said 2D projections having a unique projection geometry of the X-ray source and the X-ray receiver at a point in time at which that 2D projection is obtained, said carrier and said holder means having a mechanical instability associated therewith which precludes accurate identification at the projection geometry via said carrier and said holder means;

at least one first transmission device mounted to as to be co-movable with said X-ray source, said at least one first transmission device emitting non-ionizing radiation;

at least one second transmission device mounted so as to be co-movable with said X-ray receiver, said at least one second transmission device emitting non-ionizing radiation;

a mount that is stationarily disposed relative to said X-ray source and said X-ray receiver and said holder means;

at least one receiver device disposed at said mount for receiving said non-ionizing radiation from said at least one first transmission device and said at least one second transmission device, said at least one receiver device emitting an electrical signal corresponding to said non-ionizing radiation received by said at least one receiver device; and computer means supplied with said signal for identifying said respective projection geometries therefrom, and for calculating said plurality of 2D projections, and for reconstructing a 3D image of said examination subject from said plurality of 2D projections.

2. An X-ray exposure system as claimed in claim 1 wherein said at least one first transmission device and said at least one second transmission device each radiates said non-ionizing radiation with a directional characteristic, and wherein said X-ray exposure system comprises two reception devices disposed at said means for mounting for respectively receiving said non-ionizing radiation from said at least one first transmission device and said at least one second transmission device.

3. An X-ray exposure system as claimed in claim 2 wherein each of said two reception devices has a directional reception characteristic, the respective directional reception characteristics of said two reception devices being individually oriented toward said at least one first transmission device and said at least one second transmission device.

4. An X-ray exposure system as claimed in claim 1 wherein said at least one first transmission device emits non-ionizing radiation at a frequency different from a frequency of the non-ionizing radiation emitted by said at least one second transmission device.

5. An X-ray exposure system as claimed in claim 1 wherein said computer means comprises means for identifying the respective projection geometries from respective transit times of said non-ionizing radiation respectively from said at least one first transmission device to said at least one reception device and from said at least one second transmission device to said at least one reception device, and further comprising means for measuring ambient temperature which emits an ambient temperature signal supplied to said computer means, and said computer means comprising means for taking said ambient temperature into account in calculating said transit times.

6. An X-ray exposure system as claimed in claim 1 wherein each of said at least one first transmission device and said at least one second transmission device emit acoustic waves as said non-ionizing radiation, and wherein said at least one reception device comprises an acoustic wave receiver.

7. An X-ray exposure system as claimed in claim 6 wherein each of said at least one first transmission device and said at least one second transmission device emits ultrasound as said non-ionizing radiation, and wherein said at least one reception device comprises an ultrasound receiver.

8. An X-ray exposure system as claimed in claim 1 wherein each of said at least one first transmission device and said at least one second transmission device emits microwaves as said non-ionizing radiation, and wherein said at least one reception device comprises a microwave receiver.

9. An X-ray exposure system as claimed in claim 1 wherein each of said at least one first transmission device and said at least one second transmission device emits light as said non-ionizing radiation, and wherein said at least one receiver comprises a light receiver.

10. An X-ray exposure system as claimed in claim 1 wherein said carrier comprises a C-arm having opposite ends at which said X-ray source and said X-ray receiver are respectively mounted.

11. An X-ray exposure system comprising:

a n X-ray source which emits an X-ray beam;

an X-ray receiver on which said X-ray beam is incident;

a carrier to which said X-ray source and said X-ray receiver are mounted;

holder means to which said carrier is movably mounted for moving said X-ray source and said X-ray transmitter relative to an examination subject for obtaining a plurality of successive 2D projections of said examination subject respectively from a plurality of different projection directions, each of said 2D projections having a unique projection geometry of the X-ray source and the X-ray transmitter at a point in time at which that 2D projection is obtained, said carrier and said holding means having a mechanical instability associated therewith which includes accurate identification at the projection geometry via said carrier and said holder means;

at least one first receiver device mounted to as to be co-movable with said X-ray source, said at least one first receiver device receiving non-ionizing radiation;

at least one second receiver device mounted so as to be co-movable with said X-ray transmitter, said at least one second receiver device receiving non-ionizing radiation;

a mount that is stationarily disposed relative to said X-ray source and said X-ray receiver and said holder means;

at least one transmitter device disposed at said mount for emitting said non-ionizing radiation to said at least one first receiver device and said at least one second receiver device, said at least one receiver device emitting a signal; and computer means supplied with said signal for identifying said respective projection geometries therefrom, and for calculating said plurality of 2D projections, and for reconstructing a 3D image of said examination subject from said plurality of 2D projections.

12. A X-ray exposure system as claimed in claim 11 wherein said at least one first receiver device and said at least one second receiver device each receives said non-ionizing radiation with a directional characteristic, and wherein said X-ray exposure system comprises two transmitter devices disposed at said means for mounting for respectively emitting said non-ionizing radiation to said at least one first receiver device and said at least one second receiver device.

13. An X-ray exposure system as claimed in claim 12 wherein each of said two transmitter devices has a directional emission characteristic, the respective directional emission characteristics of said two transmitter devices being individually oriented toward said at least one first receiver device and said at least one second receiver device.

14. An X-ray exposure system as claimed in claim 11 wherein said at least one first receiver device receives non-ionizing radiation at a frequency different from a frequency of the non-ionizing radiation received by said at least one second receiver device.

15. An X-ray exposure system as claimed in claim 11 wherein said computer means comprises means for identifying the respective projection geometries from respective transit times of said non-ionizing radiation respectively from said at least one first receiver device to said at least one transmitter device and from said at least one second receiver device to said at least one transmitter device, and further comprising means for measuring ambient temperature which emits an ambient temperature signal supplied to said computer means, and said computer means comprising means for taking said ambient temperature into account in calculating said transit times.

16. An X-ray exposure system as claimed in claim 11 wherein each of said at least one first receiver device and said at least one second receiver device receives acoustic waves as said non-ionizing radiation, and wherein said at least one transmitter device comprises an acoustic wave transmitter.

17. An X-ray exposure system as claimed in claim 16 wherein each of said at least one first receiver device and said at least one second receiver device receives ultrasound as said non-ionizing radiation, and wherein said at least one transmitter device comprises an ultrasound transmitter.

18. An X-ray exposure system as claimed in claim 11 wherein each of said at least one first receiver device and said at least one second receiver device receives microwaves as said non-ionizing radiation, and wherein said at least one transmitter device comprises a microwave transmitter.

19. An X-ray exposure system as claimed in claim 11 wherein each of said at least one first receiver device and said at least one second receiver device receives light as said non-ionizing radiation, and wherein said at least one transmitter device comprises a light transmitter.

20. An X-ray exposure system as claimed in claim 11 wherein said carrier comprises a C-arm having opposite ends at which said X-ray source and said X-ray transmitter are respectively mounted.

* * * * *